United States Patent [19]

Bentley

[11] 4,308,259
[45] Dec. 29, 1981

[54] PENICILLIN DERIVATIVES

[75] Inventor: Peter H. Bentley, Horsham, England

[73] Assignee: Beecham Group Limited, England

[21] Appl. No.: 121,175

[22] Filed: Feb. 13, 1980

[30] Foreign Application Priority Data

Mar. 1, 1979 [GB] United Kingdom ............... 07302/79
Jul. 25, 1979 [GB] United Kingdom ............... 25983/79

[51] Int. Cl.³ ..................... A61K 31/67; A61K 31/43; C07D 499/46; C07F 9/65
[52] U.S. Cl. .................................. 424/200; 260/239.1; 424/271
[58] Field of Search ..................... 260/239.1; 424/200, 424/271

[56] References Cited

U.S. PATENT DOCUMENTS

| 3,966,710 | 6/1976 | McFarland et al. | 260/239.1 |
| 4,048,158 | 9/1977 | Sugimoto et al. | 260/239.1 |
| 4,057,544 | 11/1977 | Sugimoto et al. | 260/239.1 |
| 4,060,530 | 11/1977 | Howarth et al. | 260/239.1 |
| 4,185,014 | 1/1980 | Taylor et al. | 260/239.1 |
| 4,197,240 | 4/1980 | Nudelman et al. | 260/239.1 |

FOREIGN PATENT DOCUMENTS 1339007 11/1973 United Kingdom .

Primary Examiner—Natalie Trousof
Assistant Examiner—Vera C. Clarke
Attorney, Agent, or Firm—Jacobs & Jacobs

[57] ABSTRACT

A penicillin of formula (I) or a pharmaceutically acceptable salt or in vivo hydrolysable ester thereof:

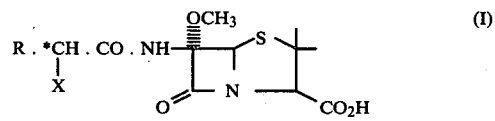

wherein R is $C_{1-6}$ alkyl; an optionally substituted 5-membered heterocyclic ring containing one or two heteroatoms selected from oxygen, sulphur and nitrogen; phenyl; mono-substituted phenyl where the substituent is halogen, hydroxy, $C_{1-6}$ alkoxy, nitro, amino, $C_{1-6}$ alkyl, or $C_{1-6}$ haloalkyl, $C_{1-6}$ alkylcarbonyloxy, or $C_{1-6}$ alkyl sulphonylamino; or di-substituted phenyl where the substituents are selected from hydroxy, halogen, methoxy, acetoxy and amino; and X represents a group of formula:

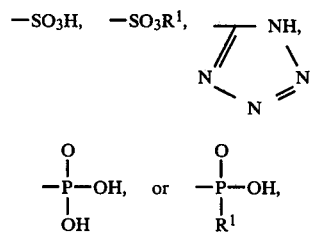

wherein $R^1$ represents $C_1$ to $C_6$ alkyl, or $C_1$ to $C_6$ alkoxy.

Their preparation and use is described.

13 Claims, No Drawings

PENICILLIN DERIVATIVES

This invention relates to a class of penicillin derivatives which have antibacterial activity and are of value in the treatment of infections in animals, including man and poultry, caused by a wide range of organisms, particularly Gram-negative organisms. In particular the invention relates to a class of 6α-methoxy penicillin derivatives having an acidic function in the side-chain. The invention also relates to a process for the preparation of such compounds, and to pharmaceutical compositions comprising them.

British Patent Specification No. 1,339,007 discloses inter alia a class of 6-substituted acylamino penicillins of general formula (A):

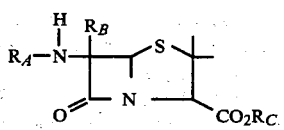

where $R_A$ represents an acyl group, $R_B$ is hydroxy or mercapto radical, a substituted or unsubstituted methoxy, ethoxy, methyl, ethyl, methylthio, or ethylthio radical, a carbamoyloxy, carbamoylthio, $C_{1-6}$ alkanoyloxy, $C_{1-6}$ alkanoylthio, cyano or carboxy radical or a derivative of a carboxy radical such as carbamoyl and $R_C$ is a hydrogen atom or a pharmaceutically acceptable esterifying radical or cation.

Our British Pat. No. 1,538,052 discloses a small class of 6αmethoxy penicillin derivatives having a carboxyl function in the side-chain.

We have now found a further class of compounds which have a high level of antibacterial activity compared to the broad class of compounds disclosed in British Pat. No. 1,339,007.

According to the present invention there is provided a compound of formula (I) or a pharmaceutically acceptable salt or in vivo hydrolysable ester thereof:

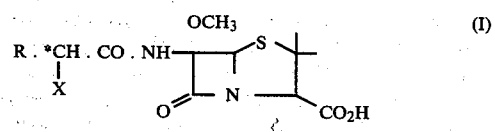

wherein R is $C_{1-6}$ alkyl; an optionally substituted 5-membered heterocyclic ring containing one or two heteroatoms selected from oxygen, sulphur and nitrogen; phenyl; mono-substituted phenyl where the substituent is halogen, hydroxy, $C_{1-6}$ alkoxy, nitro, amino, $C_{1-6}$alkyl, $C_{1-6}$haloalkyl, $C_{1-6}$alkylcarbonyloxy, or $C_{1-6}$alkyl sulphonylamino (for example $-NHSO_2CH_3$); or di-substituted phenyl where the substituents are selected from hydroxy, halogen, methoxy, acetoxy and amino; and X represents a group of formula:

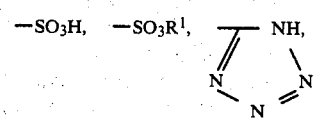

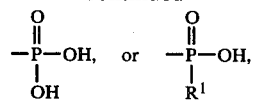

wherein $R^1$ represents $C_1$ to $C_6$ alkyl, or $C_1$ to $C_6$ alkoxy.

The compounds of the present invention include the pharmaceutically acceptable esters of compound (I) which hydrolyse readily in the human body to produce the parent acid, for example acyloxyalkyl groups such as acetoxymethyl, pivaloyloxymethyl, α-acetoxyethyl, α-acetoxybenzyl and α-pivaloyloxyethyl groups; alkoxy-carbonyloxyalkyl groups, such as ethoxycarbonyloxymethyl and α-ethoxycarbonyloxyethyl; dialkylaminoalkyl groups such as dimethylaminomethyl, dimethylaminoethyl, diethylaminomethyl or diethylaminoethyl; and lactone groups such as phthalidyl or dimethoxyphthalidyl.

Suitable salts of the compound of formula (I) include salts of the 3-carboxylic acid group and also of a sulpho or phospho group when present as group X. Salts include metal salts, e.g. aluminium, alkali metal salts such as sodium or potassium, alkaline earth metal salts such as calcium or magnesium, and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydro-abietylamine, N,N'-bisdehydroabietylethylenediamine, or bases of the pyridine type such as pyridine, collidine or quinoline, or other amines which have been used to form salts with known penicillins.

The carbon atom marked * in formula (I) is asymmetric so that the compounds may exist as two optically active diastereoisomers. In general that prepared from the D-side chain exhibits the highest antibacterial activity.

Suitably the group X is $-SO_3H$.

Suitably R is phenyl; mono-substituted phenyl where the substituent is fluorine, chlorine, hydroxy, methoxy, nitro, amino, acetoxy or trifluoromethyl; or di-substituted phenyl where the substituents are selected from acetoxy and methoxy.

Suitable $C_{1-6}$ alkyl groups for the groups for the groups R and $R^1$ include methyl, ethyl, n- and iso-propyl, n-, iso-, sec- and tert-butyl.

Suitable 5-membered heterocyclic rings for the group R include furyl, thienyl, oxazolyl, thiazolyl, isoxazolyl, isothiazolyl, imidazolyl; each such group may be substituted by various groups for example halogen, hydroxy, amino, or $C_{1-6}$ alkyl. Particular examples of such groups include thienyl and 2-aminothiazolyl.

Specific examples of the group R include phenyl, thienyl, p-hydroxyphenyl and p-aminophenyl.

Specific compounds within this invention include the following:

6,α-methoxy-6,β(2-O-methylphosphono-2-
phenylacetamido) penicillanic acid (i.e. R=phenyl,

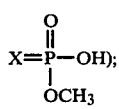

6,α-methoxy-6,β-[D,L-2-sulpho-2-phenylacetamido] penicillanic acid (i.e. R=phenyl, X=SO₃H);

6,α-methoxy-6,β-[D,L-2-sulpho-2-thien-3'-ylacetamido] penicillanic acid (i.e. R=3-thienyl, X=SO₃H);

6,α-methoxy-6,β-[D,L-2-tetrazol-5'-yl-2-phenylacetamido] penicillanic acid (i.e. R=phenyl, X=5-tetrazolyl);

6,α-methoxy-6,β-[D,L-2-phospho-2-phenylacetamido] penicillanic acid (i.e. R=phenyl, X=-P(O)(OH)₂);

6,β-[D,L-2-iso-butylsulpho-2-thien-3'-ylacetamido];

6,α-methoxy penicillanic acid (i.e. R=3-thienyl, X=SO₃Buⁱ);

6,α-methoxy-6,β-[D,L-2-methylphosphino-2-phenylacetamido] penicillanic acid (i.e. R=phenyl,

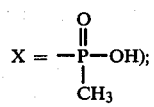

6,α-methoxy-6,β-[D,L-2-sulpho-2-p-aminophenylacetamido] penicillanic acid (i.e. R=p-aminophenyl, X=SO₃H);

6,α-methoxy-6,β-[D,L-2-sulpho-2-p-aminophenylacetamido] penicillanic acid;

6,β-[2-(4-acetoxyphenyl)-2-sulphoacetamido]-6,α-methoxypenicillanic acid;

6,β-[2-(4-hydroxyphenyl)-2-sulphoacetamido]-6,α-methoxypenicillanic acid;

6,β-[2-(2-fluorophenyl)-2-sulphoacetamido]-6,α-methoxypenicillanic acid;

6,β-[2-(2-chlorophenyl)-2-sulphoacetamido]-6,α-methoxypenicillanic acid;

6,β-[2-(4-acetoxy-3-methoxyphenyl)-2-sulphoacetamido]-6,α-methoxypenicillanic acid;

6,β-[2-(3-chlorophenyl)-2-sulphoacetamido]-6,α-methoxypenicillanic penicillanic acid;

6,α-methoxy-6,β-[2-(4-methylphenyl)-2-sulphoacetamido] penicillanic acid;

6,α-methoxy-6,β-(2-sulpho)pentanoamido penicillanic acid;

6,α-methoxy-6,β-(2-sulpho)propanoamido penicillanic acid;

6,α-methoxy-6,β-(2-sulpho)hexanoamido penicillanic acid;

6,α-methoxy-6,β-(2-sulpho)butyramido penicillanic acid;

6,α-methoxy-6,β-(4-methyl-2-sulpho)butyramido penicillanic acid;

6,α-methoxy-6,β-[2-(4-nitrophenyl)-2-sulphoacetamido] penicillanic acid;

6,α-methoxy-6,β-[2-(3-methylphenyl)-2-sulphoacetamido] penicillanic acid;

6,β-[2-(4-chlorophenyl)-2-sulphoacetamido]-6,α-methoxypenicillanic acid;

6,α-methoxy-6,β-[2-(4-trifluoromethylphenyl)-2-sulphoacetamido] penicillanic acid; and 6,α-[2-(3-aminophenyl)-2-sulphoacetamido]-6,α-methoxypenicillanic acid.

The compounds of formula (I) may be prepared by reacting a compound of formula (II):

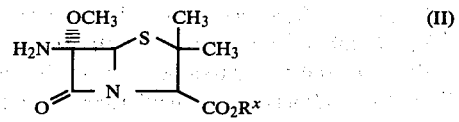

wherein the amino group is optionally substituted with a group which permits acylation to take place, and wherein $R^x$ is hydrogen or a carboxyl-blocking group, with an N-acylating derivative of an acid of formula (III):

wherein R and X are as defined with respect to formula (I) above; and thereafter, if necessary, carrying out one or more of the following steps:

(i) removing any carboxyl-blocking group $R^x$;
(ii) removing any substituent on the amide group;
(iii) converting the product into a salt or in vivo hydrolysable ester thereof.

Suitable groups which permit acylation to take place and which are optionally present on the amino group of the starting material of the formula (II) include N-silyl, N-stannyl and N-phosphorous groups, for example trialkylsilyl groups such as trimethylsilyl, trialkyltin groups such as tri-n-butyltin, groups of formula —P.-$R^aR^b$ wherein $R^a$ is an alkyl, haloalkyl, aryl, aralkyl, alkoxy, haloalkoxy, aryloxy, aralkyloxy or dialkylamino group, $R^b$ is the same as $R^a$ or is halogen or $R^a$ and $R^b$ together form a ring; suitable such phosphorus groups being —P(OC₂H₅)₂, —P(C₂H₅)₂,

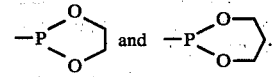

Suitable carboxyl-blocking derivatives for the group —CO₂$R^x$ in formula (II) include salts, ester, and anhydride derivatives of the carboxylic acid. The derivative is preferably one which may readily be cleaved at a later stage of the reaction. Suitable salts include tertiary amine salts, such as those with tri-loweralkylamines, N-ethylpiperidine, 2,6-lutidine, pyridine, N-methylpyrrolidine, dimethylpiperazine. A preferred salt is with triethylamine.

Suitable ester-forming carboxyl-blocking groups are those which may be removed under conventional conditions. Such groups for $R^x$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, p-toluenesulphonylethyl, methoxymethyl, a silyl, stannyl or phosphorus-containing group, such as described above, an oxime radical of formula —N=CHR° where R° is aryl or heterocyclic, or an in vivo hydrolyzable ester radical such as defined above.

The carboxyl group may be regenerated from any of the above esters by usual methods appropriate to the particular $R^x$ group, for example, acid - and base - catalysed hydrolysis, or by enzymically - catalysed hydrolysis, or by hydrogenation.

A reactive N-acylating derivative of the acid (III) is employed in the above process. The choice of reactive derivative will of course be influenced by the chemical nature of the substituents of the acid.

Suitable N-acylating derivatives include an acid halide, preferably the acid chloride or bromide. Acylation with an acid halide may be affected in the presence of an acid binding agent for example tertiary amine (such as triethylamine or triethylamine or dimethylaniline), an inorganic base (such as calcium carbonate or sodium bicarbonate) or an oxirane, which binds hydrogen halide liberated in the acylation reaction. The oxirane is preferably a $(C_{1-6})$—1,2-alkylene oxide - such as ethylene oxide or propylene oxide. The acylation reaction using an acid halide may be carried out at a temperature in the range $-50°$ C. to $+50°$ C., preferably $-20°$ C. to $+20°$ C., in aqueous or non-aqueous media such as aqueous acetone, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (III) or a salt thereof with a halogenating (e.g. chlorinating or brominating) agent such as phosphorus pentachloride, thionyl chloride or oxalyl chloride.

Alternatively, the N-acylating derivative of the acid (III) may be symmetrical or mixed anhydride. Suitable mixed anhydrides are alkoxyformic anhydrides, or anhydrides with, for example carbonic acid monoesters, trimethyl acetic acid, thioacetic acid, diphenylacetic acid, benzoic acid, phosphorus acids (such as phosphoric or phosphorous acids), sulphuric acid or aliphatic or aromatic sulphonic acids (such as p-toluenesulphonic acid). The mixed or symmetrical anhydrides may be generated using N-ethoxycarbonyl-2-ethoxy-1,2-dihydroquinoline. When a symmetrical anhydride is employed, the reaction may be carried out in the presence of 2,4-lutidine as catalyst.

Alternative N-acylating derivatives of acid (III) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol or 8-hydroxyquinoline; or amides such as N-acylsaccharins or N-acylphthalimides; or an alkylidene iminoester prepared by reaction of the acid (III) with an oxime.

Other reactive N-acylating derivatives of the acid (III) include the reactive intermediate formed by reaction in situ with a condensing agent such as a carbodiimide, for example N,N-diethyl-, dipropyl- or diisopropyl-carbodiimide, N,N'-di-cyclohexylcarbodiimide, or N-ethyl-N'-γ-dimethylaminopropylcarbodiimide; a suitable carbonyl compound, for example N,N'-carbonyldiimidazole or N,N'-carbonylditriazole; an isoxasolinium salt, for example N-ethyl-5-phenylisoxazolinium-3-sulphonate or N-t-butyl-5-methylisoxazolinium perchlorate; or an N-alkoxycarbonyl-2-alkoxy-1,2-dihydroquinoline, such as N-ethoxycarbonyl-2-ethoxy-1,2-dihydroquinoline. Other condensing agents include Lewis acids (for example $BBr_3$ —$C_6H_6$); or a phosphoric acid condensing agent such as diethylphosphorylcyanide. The condensation reaction is preferably carried out in an organic reaction medium, for example methylene chloride, dimethylformamide, acetonitrile, alcohol, benzene, dioxan, or tetrahydrofuran.

The starting material of formula (II) is disclosed in British Pat. No. 1,339,007.

Compounds of formula (I) may also be prepared by reacting a compound of formula (IV):

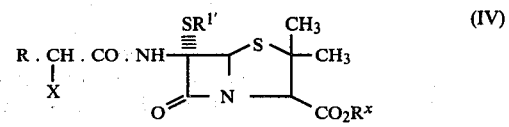

wherein R, X and $R^x$ are as defined above and $R^{1'}$ is $C_1$ to $C_6$ alkyl or benzyl; with methanol in the presence of a metal ion, such as mercury, lead, silver, cadmium, thallium, tellurium or bismuth.

This reaction may generally be carried out at a temperature of from $-50°$ C. to $+25°$ C., but is conveniently carried out between $-5°$ C. and $+25°$ C. Any suitable solvent may be employed. It is generally convenient however to use methanol as the solvent. Preferably $R^{1'}$ in formula (IV) represents methyl.

Compounds of formula (I) may also be prepared by:
(a) treating a compound of formula (V):

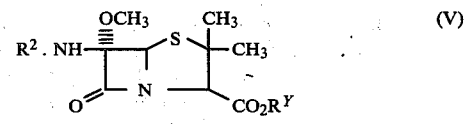

wherein $R^y$ is a carboxyl-blocking group, and $R^2$ is an acyl group, in particular an acyl group derived from the side-chain of a natural penicillin, such as benzyl penicillin or phenoxymethyl penicillin; with an agent forming an imino halide;

(b) treating the imino halide with a compound to introduce a group $QR_f$ on the imino carbon atom, wherein Q is oxygen, sulphur or nitrogen and $R_f$ is an alkyl group of from 5 to 14 carbon atoms, to form an iminoether, iminothioether, or amidine (when Q is O, S, or N respectively);

(c) treating with water; and (d) optionally removing the carboxyl-blocking group $R^y$.

A suitable agent for preparing an imino halide is an acid halide in the presence of an acid binding agent such as a tertiary amine, e.g. pyridine, triethylamine, or N,N-dimethylaniline. Examples of suitable acid halides are phosphorus pentachloride, phosgene, phosphorous pentabromide, phosphorus oxychloride, oxalyl chloride and p-toluene sulphonic acid chloride. Phosphorus pentachloride and phosphorus oxychloride are preferred. The reaction may be conducted under cooling, preferably at temperatures from $0°$ C. to $-30°$ C. when phosphorus pentachloride is employed. The amount of the tertiary amine is preferably 3–5 mols per mol of phosphorus pentachloride. It is also preferably to use the phosphorus halide in an amount slightly in excess of that of the starting material.

The resulting imino compounds are then treated to introduce a $-QR_f$ group onto the imino carbon atom. This is preferably effected by reacting the imino halide with a corresponding alcohol. Examples of suitable alcohols for reaction with the imino halide are aliphatic alcohols containing from 1 to 12 carbon atoms, preferably 1 to 5 carbon atoms, such as methanol, ethanol, propanol, isopropyl alcohol, amyl alcohol and butyl alcohol, and aralkyl alcohols such as benzyl alcohol and 2 - phenylethanol.

The reaction of the alcohol with the imino halide is preferably effected in the presence of an acid binding agent, such as a tertiary amine, preferably pyridine, and the reaction is usually carried out without isolating the imino halide from the reaction mixture.

Finally, the product is treated with water. The water treatment may be conducted together with the isolation of the desired material. That is the reaction mixture may be added to water or a saturated aqueous solution of sodium chloride and then the aqueous layer formed is separated from the organic solvent layer.

The antibiotic compounds according to the invention may be formulated for administration in any convenient way for use in human or veterinary medicine, by analogy with other antibiotics, and the invention therefore includes within its scope a pharmaceutical composition comprising a compound of formula (I) above together with a pharmaceutical carrier or excipient.

The compositions may be formulated for administration by any route, such as oral, topical or parenteral. The compositions may be in the form of tablets, capsules, powders, granules, lozenges, creams of liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maizestarch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminum stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, agents such as a local anesthetic, preservative and buffering agents can be dissolved in the vehicle. To enhance the stability, the composition can be frozen after filling into the vial and the water removed under vaccuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg. of the active ingredient. The dosage as employed for adult human treatment will preferably range from 100 to 3000 mg. per day, for instance 1500 mg. per day depending on the route and frequency of administration.

The compound of formula (I) may be the sole therapeutic agent in the compositions of the invention or a combination with other antibiotics may be employed. Advantageously the compositions also comprise a compound of formula (VI) or a pharmaceutically acceptable salt or ester thereof:

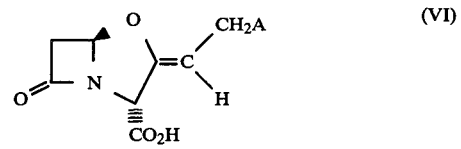

wherein A is hydroxyl, substituted hydroxyl, thiol, substituted thiol, amino, mono- or di-hydrocarbylsubstituted amino, or mono- or di-acylamino.

The following Examples illustrate the preparation of some of the compounds of this invention.

EXAMPLE 1

6α-Methoxy-6,β-(2-phenyl-2-sulphoacetamido) penicillanic acid (disodium salt)

(a) Benzyl 6,α-methylthio-6,β-(2-phenyl-2-sulphoacetamido) penicillanate

2-Sulpho-2-phenylacetyl chloride (4.45 g, 19 mmole) in ether (40 ml) was added dropwise to a stirred solution of benzyl 6,β-amino-6,α-methylthio penicillanate (6.69 g 19 mmole) and triethylamine (7.5 ml) in THF (25 ml), cooled in an ice bath. The ice bath was removed after 15 minutes then after a further 45 minutes ethyl acetate (150 ml) and water (25 ml) were added. The organic phase was collected, washed with saturated brine (2×25 ml), dried and evaporated to give the crude triethylammonium salt. This in water (20 ml) was passed through a column of 'Amberlite IR-120 (Na+) resin' to give, after evaporation of the water, the crude sodium salt which was purified by chromatography on silica eluting with 10% methanol in chloroform to give the sodium salt of the title compound, 3.38 g, 35%, $\mu_{max}(CHCl_3)$ 1780, 1745, 1678, 1250 and 1180 cm$^{-1}$, δ(CDCl$_3$) 1.25, 1.30 (6H, 2×s, 2×2CH$_3$), 2.14, 2.20 (3H, 2×s, SCH$_3$), 4.48, 4.50 (1H, 2×s, 3H), 5.20 (2H, s, OC$\underline{H}_2$Ph), 5.3–5.5 (2H, m, C$\underline{H}$CONH and 5H), 7.1–7.9 (11H, m, 2×Ph and CONH).

(b) Benzyl 6,α-methoxy-6,β-(2-phenyl-2-sulphoacetamido) penicillanate

Benzyl 6,α-methylthio-6,β-(2-phenyl-2-sulphoacetamido) penicillanate sodium salt (0.57 g, 1 mmole) in methanol (15 ml) was treated with mercuric acetate (0.32 g, 1 mmole), stirred for 1.5 hours then evaporated to dryness. Chloroform (25 ml) was added to the residue, the mixture filtered, the filtrate evaporated to dryness and the residue dissolved in water (10 ml) then passed through a column of 'Amberlite IR-120 (Na+) resin'. Removal of the water gave the crude sodium salt which was chromatographed on silica in 10% methanol in chloroform to give the sodium salt of the title compound, 0.29 g, 53%, $\nu_{max}$ (CHCl$_3$) 1780, 1745, 1680, 1260 and 1180 cm$^{-1}$, δ(CDCl$_3$) 1.25, 1.30 (6H, 2×s, 2×2CH$_3$) 3.64, (3H, s, OCH$_3$), 4.53 (1H, s, 3H), 4.94, 5.02 (1H, 2×s, CHCONH), 5.24 (2H, s, OCH$_2$Ph), 5.60 (1H, s, b 5H), 7.17–7.80 (11H, m, 2×Ph and CONH).

(c) Disodium 6,α-methoxy-6,β-(2-phenyl-2-sulphoacetamido) penicillanate

Benzyl 6,α-methoxy-6,β-(2phenyl-2-sulphoacetamido) penicillanate sodium salt (1.3 g, 2.4 mmole) in water (20 ml) containing sodium bicarbonate (0.19 g, 2.4 mmole) was hydrogenated in the presence of 10% palladium on carbon (1.3 g) for 15 minutes. The catalyst was filtered off and the filtrate evaporated to yield the title compound, 0.91 g, 78%, $\nu_{max}$(KBr) 3800–2700, 1762, 1677, 1606, 1250, 1210 and 1043 cm$^{-1}$, δ[(CD$_3$)$_2$SO]1.24–1.50 (6H, m, 2×2CH$_3$), 3.40 (3H, s, OCH$_3$), 3.92, 4.00 (1H, 2×s, 3H), 4.46, 4.76 (1H, 2×s, CHCONH), 5.33, 5.40 (1H, 2×s, 5H), 7.15–7.70 (5H, m, Ph), 9.39 (1H, s, CONH).

EXAMPLE 2

6,α-Methoxy-6,β-(2-phenyl-2-sulphoacetamido)penicillanic acid (disodium salt)

(a) Benzyl 6,α-methoxy-6,β-(2-phenyl-2-sulphoacetamido) penicillanate

Benzyl 6,β-amino-6,α-methoxypenicillante (2.5 g, 7.4 mmole) was acylated with 2-sulpho-2-phenylacetyl chloride (1.74 g, 7.4 mmole) by the method described in Example 1 (a) to give the chromatographed sodium salt of the title compound 1.31 g, 32%., identical with that prepared in Example 1 (b).

(b) The above product was converted to disodium 6,α-methoxy-6,β-(2-phenyl-2-sulphoacetamido)penicillanate by the procedure described in Example 1(c).

EXAMPLE 3

6,β-(2-Isobutoxysulphonyl-2-phenylacetamido)-6α-methoxy penicillanic acid (sodium salt)

(a) Benzyl 6,β-(2-isobutoxysulphonyl-2-phenylacetamido)-6,α-methylthio-penicillanate 2-isoButoxysulphonyl-2-phenylacetyl chloride (0.75 g) in dichloromethane (10 ml) was added dropwise to an ice cooled solution of benzyl 6,β-amino-6,α-methylthiopenicillanate (1.02 g) and pyridine (0.25 ml) in dichloromethane (20 ml). After 1.5 hours the solution was washed with dilute sodium bicarbonate solution (2×50 ml), dilute hydrochloric acid (50 ml) and water (50 ml), dried and evaporated to give the title compound, 1.42 g, 90%. $\nu_{max}$(CHCl$_3$)3350, 1780, 1745 and 1690 cm$^{-1}$. δ(CDCl$_3$) 0.91 (6H, d, J 7 Hz, CH(CH$_3$)$_2$), 1.35 (6H, m, 2×2CH$_3$) 2.00 (1H, m, CH$_2$CH(CH$_3$)$_2$), 2.28 (3H, bs, SCH$_3$), 4.95 (2H, d, J 6 Hz, SO$_3$CH$_2$CH), 4.43 (1H, bs, 3H), 5.19 (2H, s, OCH$_2$Ph), 5.24 (1H, s, 5H), 5.57 (1H bs, CHCONH), 7.2–7.8 (10H, m, 2×Ph), 7.93, 8.03 (1H, 2×s, CONH).

(b) Benzyl 6,β-(2-isobutoxysulphonyl-2-phenylacetamido)-6,α-methoxypenicillanate Benzyl 6,β-(2-isobutoxysulphonyl-2-phenylacetamido)-6,α-methylthio-penicillanate (1.42 g) in methanol (20 ml) at 0° was treated with mercuric acetate (0.75 g) in methanol (14 ml), stirred for 10 minutes, evaporated to dryness and the residue dissolved in chloroform (25 ml). The chloroform solution was washed with water (2×20 ml) and brine (25 ml), dried and evaporated to a foam which was chromatographed on silica, eluting with 20% ethyl acetate in light petroleum (b.p. 60°–80°) to give the title compound, 1.20 g, 90%. $\nu_{max}$(CHCl$_3$) 3350, 1780, 1745 and 1700 cm$^{-1}$, δ(CDCl$_3$) 0.87 (6H, d, J 7 Hz, CH(CH$_3$)$_2$), 1.1–1.4 (6H, m, 2×2CH$_3$), 1.95 (1H, m, CH$_2$CH(CH$_3$)$_2$), 3.37, 3.48 (3H, 2×s, OCH$_3$), 3.95 (2H, d, J 6 Hz, SO$_3$CH$_2$CH), 4.38, 4.46 (1H, 2×s, 3H), 5.17 (2H, s, OCH$_2$Ph), 5.30 (1H, s, 5H), 5.61 (1H, bs, CHCONH), 7.1–7.8 (10H, m, 2×Ph), 8.15 (1H, m, CONH).

(c) Sodium 6,β-(2-isobutoxysulphonyl-2-phenylacetamido)-6,α-methoxypenicillanate Benzyl 6,β-(2-isobutoxysulphonyl-2phenylacetamido)-6,α-methoxy-penicillanate (0.59 g) in methanol (50 ml) was hydrogenated in the presence of 10% palladium on carbon (0.5 g). After 3.5 hours further catalyst (0.1 g) was added then after another hour the catalyst was removed and the filtrate evaporated to dryness. The residue was dissolved in chloroform (50 ml) and extracted with saturated sodium bicarbonate solution (3×50 ml). The combined extracts were acidified to pH 2.5 and extracted with ethyl acetate (5×50 ml). The organic extracts were washed with water (50 ml) and brine (50 ml), dried and evaporated to give the free acid of the title compound, 402 mg. This in ether (20 ml) was treated with 2N sodium 2-ethylhexanoate in 4-methylpentan-2-one (0.4 ml) and the precipitated sodium salt collected, washed with ether and dried, 393 mg, 75%, $\nu_{max}$ (KBr) 3400, 2960, 1760, 1690 and 1610 cm$^{-1}$, δ[(CD$_3$)$_2$SO]0.85 (6H, d, J 7 Hz, CH(CH$_3$)$_2$), 1.2–1.45 (6 H, m, 2×2CH$_3$), 3.05, 3.17 (3H, 2×s, OCH$_3$), 3.82 (2H d, J 6 Hz, SO$_3$CH$_2$CH), 5.33 (1H, bs, 5H), 5.84 (1H, s, CHCONH), 7.28–7.70 (5H, m, Ph), 9.87 (1H, bs, CONH).

EXAMPLE 4

6,β-[2-(4-Aminophenyl)-2-sulphoacetamido]-6,α-methoxy penicillanic acid

(a) 2-(4-Nitrophenyl)2-sulphoacetyl chloride

A solution of 4-nitrophenylacetyl chloride (2.00 g, 10 mmole) in dichloromethane (20 ml) was treated with a suspension of sulphur trioxide-dioxan complex (15 mM) in dichloroethane at 0° C. This mixture was stirred at room temperature for 18 hours and evaporated to a yellow gum, $\nu_{max}$ (CHCl$_3$) 1800 cm$^{-1}$, $\delta$(CDCl$_3$) 5.98 (1H, s, CH), 7.65–8.55 (4H, m, Ar) 13.66 (1H, s, SO$_3$H).

(b) Benzyl 6,α-methoxy-6,β-[2-(4-nitorphenyl)-2-sulphoacetamido]-penicillanate A solution of the acid chloride in dichloromethane (20 ml) was added dropwise to a solution of benzyl 6,β-amino-6,α-methoxypenicillanate (3.36 g, 10 mmole) in dichloromethane (10 ml) containing triethylamine (5 ml) at 0°–5° C. After 30 minutes at 0°–5° C. and one hour at room temperature, the bulk of the solvent was evaporated in vacuo and the resultant gum dissolved in ethyl acetate (100 ml) and water (20 ml). The phases were separated and the aqueous layer extracted with ethyl acetate (25 ml). The combined organic extracts were washed with saturated brine (50 ml) and dried over magnesium sulphate. Evaporation of the solvent in vacuo yielded a yellow foam which was further purified by chromatography on silica. The title compound (as its triethylammonium salt) was eluted with 10% methanol in chloroform. The solvents were removed and an aqueous solution was passed through a column of "Amberlite" IR-120 (Na+) resin to yield, after evaporation of the solvent, the sodium salt of the title compound as a yellow foam (4.00 g, 66.6% yield), $\nu_{max}$ (KBr) 1780, 1745, 1685, 1525, 1350, 1210, 1045, 700 cm$^{-1}$, $\delta$ [(CD$_3$)$_2$CO], 1.15–1.65 (6H, m, 2×2CH$_3$) 3.50, 3.55 (3H, 2×s, OCH$_3$), 4.49, 4.56 (1H, 2×s, 3H), 5.04, 5.32 (1H, 2×s, CHCONH). 5.24 (2H, bs, OCH$_2$) 5.51 (1H, s, 5H), 7.42 (5H, bs, Ph), 7.80–8.35 (4H, m, NO$_2$C$_6$H$_4$).

(c) Disodium 6,β-[2-(4-aminophenyl)-2-sulphoacetamido]-6,α-methoxy-penicillanate Benzyl 6,α-methoxy-6,β-[2-(4-nitrophenyl)-2-sulphoacetamido]-penicillanate sodium salt (1.2 g, 2.0 mmole) in water (150 ml) containing sodium bicarbonate (2.0 mmole) was hydrogenated in the presence of 10% palladium on charcoal (1.5 g) for 18 hours at atmospheric pressure (alternatively for 6 hours at 300 p.s.i.). The catalyst was filtered off and washed and the aqueous solution freeze-dried to give the title compound as an off-white foam (0.65 g, 70.2%), $\nu_{max}$ (KBr), 1765, 1775, 1610, $\delta$ [(CD$_3$)$_2$SO/D$_2$O] 9.35 (6H, bs, 2×2CH$_3$), 3,48, 3.51 (3H, 2×s, OCH$_3$) 3.96, 4.04 (1H, 2×s, 3H), 4.28, 4.53 (1H, 2×s, CHCONH), 5.33, 5.37 (1H, 2×s, 5H), 6.36–7.40 (4H, m, NH$_2$C$_6$H$_4$).

EXAMPLE 5

6,α-Methoxy-6,β-(-2-Phosphono-2-phenylacetamido)-penicillanic acid

(a) Benzyl 6,β-(2-dibenzylphosphono-2-phenylacetamido)-6,α-methylthio penicillanate 2-Dibenzylphosphono-2-phenylacetyl chloride (1.58 g, 3.8 mmole) in dichloromethane (10 ml) was added to an ice bath cooled solution of benzyl 6,β-amino-6,α-methylthiopenicillanate (1.51 g, 4.3 mmole) and pyridine (0.8 ml) in dichloromethane (50 ml). After one hour the solution was washed with dilute hydrochloric acid then with water, dried and evaporated to a foam. This crude product was chromatographed on silica gel and the product eluted with 25% ethylacetate in cyclohexane, 1.63 g, 59%, $\nu_{max}$ (CHCl$_3$) 1780, 1745, 1685, 1490, 1310, 1270, and 900 cm$^{-1}$, $\delta$ (CDCl$_3$) 1.25 and 1.33 (6H, 2×s, 2×2CH$_3$), 2.18 (3H, s, SCH$_3$), 4.21 and 4.25 (1H, 2×d, J 24 Hz, CHP), 4.41 (1H, s, 3H), 4.5–5.15 (4H, m, P(OCH$_2$Ph)$_2$), 5.15 (2H, s, OCH$_2$Ph), 5.51 (1H, s, 5H), 7.0–7.7 (2OH, m, 4×Ph), 7.90 and 7.95 (1H, 2×s, CONH).

(b) Benzyl 6,β-(2-dibenzylphosphono-2-phenylacetamido)-6,α-methoxypenicillanate Benzyl 6,β-(2-dibenzylphosphono-2-phenylacetamido)-6,α-methylthiopenicillanate (1.33 g, 1.8 mmole) in DMF (2 ml) and methanol (40 ml) was treated with mercuric acetate (0.58 g, 1.8 mmole) and the mixture stirred for 30 minutes. Ethyl acetate (100 ml) was added, the solution washed twice with water, once with 1% sodium sulphide solution, twice more with water and once with saturated brine then dried and evaporated to a foam. Chromatography on silica gel eluting with 30% ethylacetate in cyclohexane gave the title compound, 1.07 g, 82%, $\nu_{max}$ (CHCl$_3$) 1780, 1745, 1690, 1495, 1260 and 1000 cm$^{-1}$, $\delta$ 1.23 (6H, s, 2×2CH$_3$), 3.35 and 3.38 (3H, 2×s, OCH$_3$), 4.42 and 4.43 (1H, 2×s, 3H), 4.0–51. (5H, m, CHP/OCH$_2$)$_2$), 5.17 (2H, s, OCH$_2$Ph), 5.57 (1H, s, 5H), 7.0–7.7 (2OH, m, 4×Ph), 8.12 and 8.30 (1H, 2×s, CONH).

(c) 6,α-Methoxy-6,β-(2-phosphono-2-phenylacetamido)-penicillanic acid sodium salt Benzyl 6,β-(2-dibenzylphosphono-2-phenylacetamido)-penicillanate (1.05 g, 1.47 mmole) and sodium bicarbonate (0.37 g, 4.4 mmole) in ethanol (100 ml) and water (ca. 10 ml) were hydrogenated in the presence of 10% palladium on carbon (1.0 g) for one hour. The catalyst was filtered off and the filtrate evaporated to dryness to yield the title compound, $\nu_{max}$ (KBr) 1765, 1660, 1610, 1095 and 972 cm$^{-1}$, $\delta$ [(CD$_3$)$_2$SO+D$_2$O] 1.32 (6H, s, 2×2CH$_3$), 3.47 (3H, s, OCH$_3$), 3.98 and 4.02 (1H, 2×s, 3H), 5.38 (1H, s, 5H), 7.1–7.6 (5H, m, Ph).

EXAMPLE 6

6,α-Methoxy-6,β(2-O-Methylphosphono-2-phenylacetamido)penicillanic acid

(a) Benzyl 6,β-(2-O-methylphosphono-2-phenylacetamido)-6,α-methoxypenicillanate sodium salt 2-O-Methylphosphono-2-phenylacetic acid (2.30 g, 10 mmole) and DMF (one drop) in thionyl chloride (10 ml) were heated at 50° for one hour, evaporated to dryness, dissolved in THF (20 ml), cooled in an ice bath then treated with trimethylsilyl chloride (1.4 ml) followed dropwise by hexamethyldisilazane (0.7 ml) in THF (5 ml). The mixture was allowed to warm to room temperature then added dropwise to an ice bath cooled solution of benzyl 6,β-amino-6,α-methoxypenicillanate (3.36 g, 10 mmole) and pyridine (2 ml) in THF (20 ml). After two hours the mixture was treated with methanol (2 ml), diluted with ethyl acetate (50 ml) and washed with water (3×7.5 ml). Water (50 ml) was added and the layers mixed while dilute sodium bicarbonate was added to pH 6.7. The aqueous layer was collected, the organic layer extracted with water (20 ml) then the combined aqueous extract freeze dried to yield the title compound, 2.73 g, 48%, $\nu_{max}$ (KBr) 1780, 1745, 1675, 1205, 1060 (br) and 695 cm$^{-1}$, $\delta$ [(CD$_3$)$_2$SO] 1.25 and 1.38 (6H, 2×s, 2×2CH$_3$), 3.0–4.3 (7H, m, CHPOCH$_3$, 6 OCH$_3$), 4.52 and 4.57 (1H, 2×s, 3H), 5.20 (2H, s, OC$\underline{H}_2$Ph), 5.35 (1H, s, 5H), 7.0–7.7 (1OH, m, 2×Ph), 10.37 and 10.60 (1H, 2×s, CON$\underline{H}$).

(b) 6,α-Methoxy-6,β-(2-O-methylphosphono-2-phenylacetamido)penicillanic acid disodium salt Benzyl 6,α-methoxy-6,β-(2-O-methylphosphono-2-phenylacetamido)penicillanate sodium salt (2.66 g, 4.85 mmole) in water (50 ml) containing sodium bicarbonate (0.3 g, 3.64 mmole) was hydrogenated in the presence of 10% palladium on carbon (2.66 g) for one hour. The catalyst was filtered off and the aqueous solution freeze dried to give the title compound, 1.92 g, 82.0%, $\nu_{max}$ (KBr) 1765, 1665, 1610, 1210, 1060 and 770 cm$^{-1}$, δ (D$_2$O), 1.25, 1.35 and 1.42 (6H, 3×s, 2×2CH$_3$), 3.3–3.6 (6H, m, POCH$_3$, 6OCH$_3$), 4.16 and 4.20 (1H, 2×d, J 22 Hz, CHP), 4.18 and 4.22 (1H, 2×s, 3H), 5.46 and 5.48 (1H, s, 5 H), 7.2–7.6 (5H, m, Ph).

EXAMPLE 7

6,β-[2-(4-Acetoxyphenyl)-2-sulphoacetamido]-6,α-methoxy-penicillanic acid (a) 2-(4-Acetoxyphenyl)-2-sulphoacetyl chloride A solution of 4-acetoxyphenylacetyl chloride (1.06 g, 5.0 mmole) in dichloromethane (10 mls) was treated with a suspension of sulphur trioxide - dioxane complex (7.5 mmole) in dichloroethane at 0° C. This mixture was stirred at room temperature for eighteen hours and evaporated to afford a pale yellow gum. $\nu_{max}$ (CHCl$_3$) 1860, 1760 cm$^{-1}$.

(b) Benzyl 6,β-[2-(4-acetoxyphenyl)-2-sulphoacetamido]-6,α-methylthiopenicillanate The sodium salt of the title compound was prepared from 2-(4-acetoxyphenyl)-2-sulphoacetyl chloride (1.46 g, 5.0 mmole) and benzyl 6,β-amino-6,α-methylthiopenicillanate (1.61 g, 5 mmole) by the method outlined in Example 1(a). Yield 0.48 g, 15.2%. $\nu_{max}$ (KBr) 3680–2860, 1780, 1743, 1680, 1504, 1370, 1308, 1210, 1030 cm$^{-1}$, δ[(CD$_3$)$_2$CO] 1.30, 1.38 (6H, 2×s, 2×2CH$_3$), 2.23 (3H, s, C$\underline{H}_3$CO), 2.36 (3H, s, SC$\underline{H}_3$), 4.20, 4.25 (1H, 2×s, 3H), 4.95, 5.20 (1H, 2×s, C$\underline{H}$CONH), 5,25 (2H, s, OC$\underline{H}_2$Ph), 5.46 (1H, s, 5H), 7.00–7.82 (9H, m, Ar), 9.25 (1H, s, CHCON$\underline{H}$).

(c) Benzyl 6,β-[2-(4-acetoxyphenyl)-2-sulphoacetamido]-6,α-methoxypenicillanate

The sodium salt of the title compound was prepared from benzyl 6,β-[2-(4-acetoxyphenyl)-2-sulphoacetamido]-6,α-methylthiopenicillanate sodium salt (0.63 g, 1.00 mmole) by the method outlined in Example 1(b). Yield 0.55 g, 88.7%. $\nu_{max}$ (KBr) 3700–2900, 1780, 1750, 1685, 1565, 1505, 1202, 1042 cm$^{-1}$. δ[(CD$_3$)$_2$SO] 1.22, 1.40 (6H, 2×s, 2×2CH$_3$), 2.01 (3H, s, C$\underline{H}_3$CO), 3.40 (3H, s, OC$\underline{H}_3$), 4.45, 4.55 (1H, 2×s, 3H), 4.50, 4.80 (1H, 2×s, C$\underline{H}$CONH), 5.18 (2H, s, OCH$_2$Ph) 5.31, 5.37 (1H, 2×s, 4H), 6.90–7.6 (9H, m, Ar), 9.55 (1H, s, CHCON$\underline{H}$).

(d) Benzyl 6,β-[2-(4-acetoxyphenyl)-2-sulphoacetamido]-6,α-methoxypenicillanate

The sodium salt of the title compound was also prepared directly from 2-(4-acetoxyphenyl)-2-sulphoacetyl chloride (2.72 g, 10 mmole) and benzyl 6,β-amino-6,α-methoxypenicillanate (3.36 g, 10 mmole) by the method outlined in Example 1(a). Yield 0.49 g, 7.8%. The nmr and IR spectral data were in agreement with those listed about for Example 7(c).

(e) Disodium 6,β-[2-(4-acetoxyphenyl)-2-sulphoacetamido]-6,α-methoxypenicillanate Benzyl 6,β-[2-(4-acetoxyphenyl)-2-sulphoacetamido]-6,α-methoxypenicillanate (0.42 g, 0.68 mmole) in water (20 mls) was hydrogenated in the presence of 10% palladium on carbon for eight hours during which time the pH was adjusted to 7 by the periodic addition of dilute sodium hydrogen carbonate solution. The catalyst was filtered off and the filtrate evaporated to yield the title compound (0.26 g, 69.4%). $\nu_{max}$ (KBr) 3700–2840, 1740, 1680, 1610, 1510, 1205, 1170, 1048 cm$^{-1}$, δ[(CD$_3$)$_2$SO] 1.35 (6H, s, 2×2CH$_3$) 2.21 (3H, s, C$\underline{H}_3$COO), 3.40 (3H, s, OC$\underline{H}_3$), 3.90, 4.00 (1H, 2×s, 3H), 4.45, 4.79 (1H, 2×s, C$\underline{H}$CONH), 5.40, 5.48 (1H, 2×s, 5H), 6.92–7.6 (4H, m, Ar), 9.38 (1H, s, CHCON$\underline{H}$).

EXAMPLE 8

6,β-[2-(4-Hydroxyphenyl)-2-sulphoacetamido]-6,α-methoxypenicillanic acid (a) Benzyl 6,β-[2-(4-hydroxyphenyl)-2-sulphoacetamido]-6,α-methoxypenicillanate Benzyl 6,β-[2-(4-acetoxyphenyl)-2-sulphoacetamido]-6,α-methoxypenicillanate sodium salt (1.52 g, 2.65 mmol) was dissolved in aqueous methanol containing sodium bicarbonate (1.34 g, 16 mmole) and the pH adjusted to 9.4 with dilute sodium hydroxide. The reaction was stirred at room temperature for three hours. The solution was then adjusted to pH 7 with dilute hydrochloric acid and evaporated to afford a white solid which was redissolved in methanol, filtered and evaporated to leave the title compound. Yield 0.62 g, 41%. $\nu_{max}$ (KBr) 3700–2800, 1780, 1742, 1680, 1610, 1512, 1455, 1315, 1202, 1100, 1040 cm$^{-1}$; δ[(CD$_3$)$_2$SO] 1.25, 1.35 (6H, 2×s, 2×2 CH$_3$) 3.40 (3H, s, OC$\underline{H}_3$), 4.31, 4.46 (1H, 2×s, 3H), 4.55, 4.60 (1H, 2×s, C$\underline{H}$CONH), 5.18 (2H, s, OC$\underline{H}_2$, Ph), 5.32, 5.38 (1H, s, 5H, 6.55, 7.42 (9H, m, Ar), 9.15, 9.5 (2H, 2×br, s, —O$\underline{H}$ and CHCON$\underline{H}$).

(b) Disodium 6,β-[2-(4-hydroxyphenyl)-2-sulphoacetamido]-6,α-methoxypenicillanate Benzyl 6,β-[2-(4-hydroxphenyl)-2-sulphoacetamido]-6,α-methoxypenicillanate (0.200 g, 0.3 mmole) in water (20 ml) containing sodium bicarbonate (0.03 g, 0.35 mmole) was hydrogenated in the presence of 10% palladium on carbon for six hours. The catalyst was filtered off and the filtrate evaporated to afford a white solid which was redissolved in methanol, filtered and the filtrate evaporated to afford the title compound. Yield 0.10 g, 59.6% $\nu_{max}$ (KBr) 3700–2800, 1765, 1680, 1610, 1512, 1208, 1175, 1042 cm$^{-1}$, δ (D$_2$O) 1.18, 1.32 (6H, 2×s, 2×2CH$_3$), 3.35, 3.5 (3H, 2×s, OC$\underline{H}_3$), 3.70, 3.80 (1H, 2×s, 3H), 4.90, 5.00 (1H, 2×s, C$\underline{H}$CONH), 5.18, 4.48 (1H, 2×s, 5H), 6.81–7.52 (4H, m, Ar).

EXAMPLE 9

6,β-[2-(2-Fluorophenyl)-2-sulphoacetamido]6,α-methoxypenicillanic acid

(a) 2-(2Fluorophenyl)-2-sulphoacetylchloride

A solution of 2-(2-fluorophenyl)acetyl chloride (1.73 g, 10 mmole) in dichloromethane (20 ml) was treated with a suspension of sulphur trioxide—dioxane complex (15 mmole) in dichloroethane at 0° C. This mixture was stirred at room temperature for eighteen hours and evaporated to a yellow gum. $\nu_{max}$. (CHCl$_3$) 1805 cm$^{-1}$.

(b) Benzyl 6,β-[2-(2-fluorophenyl)-2-sulphoacetamido]-6,α-methylthiopenicillanate The triethylammonium salt of the title compound was prepared from 2-(2-fluorophenyl)-2-sulphoacetyl chloride (2.53 g, 10 mmole) and benzyl 6β-amino-6,β-methylthio-penicillanate (3.52 g, 10 mmole) by the method outlined in Example 1a. Yield 3.70 g, 55%. $\nu_{max}$. (KBr) 1780, 1740, 1685, 1490, 1235, 1205 cm$^{-1}$, δ[(CD$_3$)$_2$SO] 1.06–1.60 [15H, m, 2×2CH$_3$ and HN$^+$(CH$_2$CH$_3$)$_3$], 2.31 (3H, s, CH$_3$), 3.05 [6H, m, q, J=7 Hz, HN$^+$(CH$_2$CH$_3$)$_3$], 4.50, 4.58 (1H, 2×s, 3H), 4.81, 5.06 (1H, 2×s, CHCONH), 5.18 (2H, s, OCH$_2$Ph), 5.30, 5.35 (1H, 2×s, 5H), 7.00–7.90 (9H, m, Ar), 9.65 (1H, s, CHCONH).

(c) Benzyl 6,β-[2-(2-fluorophenyl)-2-sulphoacetamido]-6,α-methoxypenicillanate The sodium salt of the title compound was prepared from benzyl 6,β-[2-(2-fluorophenyl)-2-sulphoacetamido]-6, α-methylthiopenicillanate triethylammonium salt (3.24 g, 5.5 mmole) by the method outlined in Example 1b. Yield 1.85 g, 59%. $\nu_{max}$. (KBr) 1775, 1742, 1685, 1490, 1455, 1235, 1202, 1100, 1040 cm$^{-1}$, δ [(CD$_3$)$_2$SO] 1.25, 1.40 (6H, 2×s, 2×2CH$_3$), 2.42, 2.43 (3H, 2×s, OCH$_3$), 4.50, 4.58 (1H, 2×s, 3H), 4.81, 5.04 (1H, 2×s, CHCONH), 5.18 (2H, s, OCH$_2$Ph), 5.32, 5.38 (1H, 2 × s, 5H), 7.00–7.85 (9H, m, Ar), 9.69 (1H, s, CHCONH).

(d) Disodium 6,β-[2-(2-fluorophenyl)-2-sulphoacetamido]-6,α-methoxypenicillanate Benzyl 6,β-[2-(2-fluorophenyl)-2-sulphoacetamido]-6, α-methoxypenicillanate sodium salt (1.75 g, 3.05 mmole) in water (20 ml) containing sodium bicarbonate (0.24 g, 3.00 mmole) was hydrogenated in the presence of 10% palladium on carbon for two hours. The catalyst was filtered off and the filtrate evaporated to yield the title compound, (1.07 g, 69.2%), $\nu_{max}$. (KBr) 3700–2850, 1762, 1685, 1605, 1490, 1460, 1410, 1350, 1235, 1210, 1100, 1040 cm$^{-1}$, δ [(CD$_3$)$_2$SO] 1.35 (6H, s, 2×2CH$_3$), 3.40, 3.42 (3H, 2×s, OCH$_3$), 3.95, 4.00 (1H, 2×s, 3H), 4.80, 5.05 (1H, 2×s, CHCONH), 5.32, 5.38 (1H, 2×s, 5H), 7.00–7.88 (4H, m, Ar) 9.51 (1H, s, CHCONH).

EXAMPLE 10

6,β-[2-(2-Chlorophenyl)-2-sulphoacetamido]-6.α-methoxypenicillanic acid

(a) 2-(2-Chlorophenyl)-2-sulphoacetyl chloride

A solution of 2-(2-chlorophenyl)acetyl chloride (1.89 g, 10 mmole) in dichloromethane (20 ml) was treated with a suspension of sulphur trioxide—dioxane complex (15 mmole) in dichloroethane at 0° C. The mixture was stirred at room temperature for eighteen hours and evaporated to afford a yellow gum. $\nu_{max}$. (CHCl$_3$) 1800 cm$^{-1}$.

(b) Benzyl 6,β-[2-(2-chlorophenyl)-2-sulphoacetamido]-6,α-methoxypenicillanate The sodium salt of the title compound was prepared from 2-(2-chlorophenyl)-2-sulphoacetyl chloride (2.69 g, 10 mmole) and benzyl 6,β-amino-6,α-methoxypenicillanate (3.36 g, 10 mmole) by the method outlined in Example 1a. Yield 0.62 g, 10.5%. $\nu_{max}$. (KBr) 3700–2800, 1775, 1744, 1685, 1512, 1320, 1240, 1210, 1180, 1040 cm$^{-1}$δ [(CD$_3$)$_2$SO] 1.25, 1.40 (6H, 2×s, 2×2CH$_3$), 3.44 (3H, s, OCH$_3$), 4.52 (1H, s, 3H), 5.18 (2H, s, OCH$_2$Ph), 5.30, 5.32 (2H, 2×s, CHCONH and 5H), 7.17–7.95 (9H, m, Ar), 9.64 (1H, s, CHCONH).

(c) Disodium 6,β[2-chlorophenyl)-2-sulphoacetamido]-6,α-methoxypenicillanate Benzyl 6,β-[2-(2-chlorophenyl)-2-sulphoacetamido]-6,α-methoxypenicillanate sodium salt (0.62 g, 1.05 mmole) in 1:1 methanol:water (15 ml) containing sodium bicarbonate (0.084 g, 1.0 mmole) was hydrogenated in the presence of 10% palladium on carbon for three hours. The catalyst was filtered off and the filtrate evaporated off to yield the title compound (0.46 g, 83.8%), $\nu_{max}$. (KBr) 3700–2850, 1762, 1682, 1610, 1340, 1250, 1210, 1180, 1100, 1045 cm$^{-1}$, δ [(CD$_3$)$_2$SO] 1.38 (6H, s, 2×2CH$_3$), 3.40 (3H, s, OCH$_3$), 4.01 (1H, s, 3H), 5.28, 5.30 (2H, 2×s, CHCONH and 5H), 7.18–7.90, 7.90 (4H, m, Ar), 9.45 (1H, s, CHCONH).

EXAMPLE 11

6,β-[2-(4-Acetoxy-3-methoxyphenyl)-2-sulphoacetamido]-6, α-methoxypenicillanic acid

(a) 2-(4-Acetoxy-3-methoxyphenyl)-2-sulphoacetyl chloride

A solution of 4-acetoxy-3-methoxyphenylacetyl chloride (2.42 g, 10 mmole) in dichloromethane (20 ml) was treated with a suspension of sulphur trioxide - dioxane complex (15 mmole) dichloroethane at 0° C. This mixture was stirred at room temperature for eighteen hours and evaportated to afford a yellow gum. $\nu_{max}$. (CHCL$_3$) 1800, 1748 cm$^{-1}$.

(b) Benzyl 6,β-[2-(4-acetoxy-3-methoxyphenyl)-2-sulphoacetamido]-6,α-methylthiopenicillanate The sodium salt of the title compound was prepared from 2-(4-acetoxy-3-methoxyphenyl)-2-sulphoacetyl chloride (3.22 g, 10 mmole) and benzyl 6,β-amino-6-α-methylthiopenicillanate (3.52 g, 10 mmole) by the method outlined in Example 1a. Yield 0.81 g, 12.3%. $\nu_{max}$. (KBr) 3700–2850, 1775, 1750, 1680, 1500, 1280, 1202, 1175, 1070 cm$^{-1}$, δ [CD$_3$)$_2$SO] 1.1, 1.20 (6H, 2×s, 2×2CH$_3$), 2.05 (3H, s, SCH$_3$), 2.21 (3H, s, CH$_3$CO), 3.72 (3H, s, OCH$_3$), 4.41, 4.45 (1H, 2×s, 3H), 5.15, 5.18 (3H, 2×bs, CHCONH and OCH$_2$Ph), 5.28, 5.32 (1H, 2×s, 5H), 6.92–7.40 (8H, m, Ar), 9.67 (1H, s, CHCONH).

(c) Benzyl 6,β-[2-(4-acetoxy-3-methoxyphenyl)-2-sulphoacetamido]-6,β-methoxypenicillanate The sodium salt of the title compound was prepared from benzyl 6,β-[2-(4-acetoxy-3-methoxyphenyl)-2-sulphoacetamido]-6,β-methylthiopenicillanate sodium salt (0.79 g, 1.2 mmole) by the method outlined in Example 1b. Yield 0.46 g. 59.6%, $\nu_{max}$. (KBr) 3680–2840, 1770, 1750, 1685, 1610, 1505, 1320, 1180, 1210, 1180, 1070 cm$^{-1}$, δ [(CD$_3$)$_2$SO] 1.02, 1.18 (6H, 2×s, 2×2CH$_3$), 2.22 (3H, s, CH$_3$COO) 3.25 (3h, s, OCH$_3$), 3.75 (3H, s, OCH$_3$), 4.42, 4.52 (1H, 2×s, 3H), 5.15 (3H, br, s, CHCONH and OCH$_2$Ph), 5.30, 5.35 (1H, 2×s, 5H), 6.95–7.50 (8H, m, Ar), 9.70 (1H, s, CHCONH).

(d) Disodium 6,β-[2-(4-acetoxy-3-methoxyphenyl)-2-sulphoacetamido]-6,α-methoxypenicillanate Benzyl 6,β-[2-(4-acetoxy-3-methoxyphenyl)-2-sulphoacetamido]-6,α-methoxypenicillanate sodium salt (0.46 g, 0.71 mmole) in water (50 ml) was hydrogenated over 10% palladium on carbon for three hours. The catalyst was removed by filtration and the filtrate adjusted to pH 7 with dilute sodium bicarbonate. The solution was evaporated and the residue redissolved in methanol, filtered and evaporated to afford the title compound. Yield 0.21 g, 53.1%. $\nu_{max}$. (KBr) 3700–2820, 1760, 1670, 1605, 1500, 1370, 1177, 1212, 1170, 1070 cm$^{-1}$, δ [(CD$_3$)$_2$SO] 1.05, 1.30 (6H, 2×s, 2×2CH$_3$), 2.22 (3H, s, CH$_3$CO$_2$), 3.15, 3.20 (3H, 2×s, OCH$_3$), 3.75 (3H, s, ArOCH$_3$), 3.82 (1H, s×3H), 5.31 (2H, br. s, CHCONH and 5H), 6.95–7.40 (3H, m, Ar) 9.40 (1H, s, CHCONH).

EXAMPLE 12

6,β-[2-(3-Chlorophenyl)-2-sulphoacetamido]-6,α-methoxypenicillanic acid

(a) 2-(3-Chlorophenyl)-2-sulphoacetyl chloride

A solution of 3-chlorophenylacetyl chloride (1.89 g, 10 mmole) in dichloromethane (20 ml) was treated with a suspension of sulphur trioxide—dioxane complex (15 mmole) in dichloroethane at 0° C. The mixture was stirred at room temperature for eighteen hours and evaporated, $\nu_{max}$. (CH$_2$Cl$_2$) 1790 cm$^{-1}$.

(b) Benzyl 6,β-[2-(3-chlorophenyl)-2-sulphoacetamido]-6,α-methoxypenicillanate The sodium salt of the title compound was prepared from 2-(3-chlorophenyl)-2-sulphoacetyl chloride (2.69 g, 10 mmole) and benzyl 6,β-amino-6,α-methoxypenicillanate (3.36 g, 10 mmole) by the method outlined in Example 1a. Yield 26.3%. $\nu_{max}$. (CDCl$_3$) 1770, 1740, 1680, 1250 cm$^{-1}$, δ [(CD$_3$)CO] 1.27, 1.31, 1.48 (6H, 3×s 2×2CH$_3$), 3.50, 3.52, (3H, 2×s, OCH$_3$), 4.47, 4.53 (1H, 2×s, 3H), 4.97, 5.30 (1H, 2×s, CHCONH), 5.24 (2H, s, OCH$_2$Ph), 5.50 (1H, s, 5H), 7.15–7.90 (9H, m, Ar), 9.25, 9.33 (1H, 2×s, CONH).

(c) Disodium 6,β-[2-(3-chlorophenyl)-2-sulphoacetamido]-6,α-methoxypenicillanate Benzyl 6,β-[2-(3-chlorophenyl)-2-sulphoacetamido]-6,α-methoxypenicillanate sodium salt (1.18 g, 2.0 mmole) in water (20 ml) containing sodium bicarbonate (0.17 g, 2.0 mmole) was hydrogenated in the presence of 10% palladium on carbon for three hours. The catalyst was filtered off and the filtrate freeze-dried to yield the title compound (0.92 g, 88.5%). $\nu_{max}$. (KBr) 3450 (broad), 1765, 1680, 1605, 1210, 1040 cm$^{-1}$, δ [(CD$_3$)SO] 1.27, 1.36 (6H, 2×s, 2×2CH$_3$), 3.43, 3.50 (3H, 2×s, OCH$_3$), 3.93, 4.02 (1H, s, 3H), 4.56, 4.90 (1H, 2×s, CHCONH), 5.33, 5.43 (1H, 2×s, 5H), 7.25–7.80 (4H, m Ar), 9.44, 9.48 (1H, 2×s, CONH).

EXAMPLE 13

6,α-Methoxy-6,β-[2-(4-methylphenyl)-2-sulphoacetamido]-penicillanic acid

(a) 2-(4-Methylphenyl)-2-sulphoacetyl chloride

A solution of 4-methylphenylacetyl chloride (1.69 g, 10 mmole) in dichloromethane (20 ml) was treated with a suspension of sulphur trioxide—dioxane complex (15 mmole) in dichloromethane. The mixture was stirred at room temperature for eighteen hours and evaporated.

(b) Benzyl 6,α-methoxy-6,β-[2-(4-methylphenyl)-2-sulphoacetamido]penicillanate The sodium salt of the title compound was prepared from 2-(4-methylphenyl)-2-sulphoacetyl chloride (2.48 g, 10 mmole) and benzyl 6,β-amino-6,α-methoxypenicillanate (3.36 g, 10 mmole) by the method outlined in Example 1a. Yield 1.6 g, 28.1%. $\nu_{max}$. (CHCl$_3$) 3450 (broad), 1770, 1740, 1670, 1250, 1190 cm$^{-1}$, δ [(CD$_3$)$_2$CO] 1.27, 1.47 (6H, 2×s, 2×2CH$_3$), 3H, s, ArCH$_3$), 3.50, 3.52 (3H, 2×s, OCH$_3$), 4.50, 4.53 (1H, 2×s, 3H), 4.98, 5.27 (1H, 2×s, CHCONH), 5.27 (2H, s, OCH$_2$Ph), 5.53 (1H, s, 5H), 7.10, 7.60 (4H, ABq, J 10 Hz, Ar) 7.44 (5H, s, Ph), 9.20 (1H, s, CONH).

(c) Disodium 6,α-methoxy-6,β-[2-(4-methylphenyl)-2-sulphoacetamidopenicillanate Benzyl 6,α-methoxy-6,β-[2-(4-methylphenyl)-2-sulphoacetamidopenicillate sodium salt (1.6 g, 2.8 mmole) in water (20 ml) containing sodium bicarbonate (0.24 g, 2.8 mmole) was hydrogenated in the presence of 10% palladium on carbon for three hours. The catalyst was filtered off and the filtrate freeze-dried to yield the title compound (1.2 g, 85.1%). $\nu_{max}$. (KBr) 3450 (broad), 1770, 1680, 1610, 1210, 1040 cm$^{-1}$, δ [(CD$_3$)$_2$SO] 1.27, 1.37 (6H, 2×s, 2×2CH$_3$), 2.25 (3H, s, ArCH$_3$) 3.40 (3H, s, OCH$_3$), 3.59 (6H, s, 3H$_2$O), 3.95, 4.04 (1H, 2×s, 3H), 4.45, 4.79 (1H, 2×s, CHCONH), 5.35, 5.42 (1H, 2×s, 5H), 7.06 (2H, d, J 8Hz,

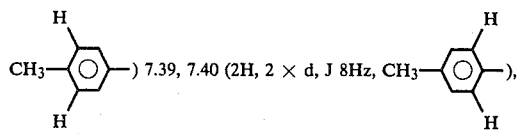

) 7.39, 7.40 (2H, 2 × d, J 8Hz, CH$_3$—⟨O⟩—), 9.36, 9.40 (1H, 2×2, CONH).

EXAMPLE 14

6,α-Methoxy-6,β-(2-sulphopentanoamido)penicillanic acid

(a) Benzyl 6,α-methoxy-6,β-(sulphopentanoamido)penicillanate

2-Sulphopentanoyl chloride (1.70 g, 8.5 mmol) in dichloromethane (5 ml) was added to a solution of benzyl 6,β-amino-6,α-methoxypenicillanate (2.85 g, 8.5 mmol) in dichloromethane (50 ml) containing triethylamine (3.6 ml) at 0° C. After thirty minutes at 0° C. and 1.5 hours at room temperature, the solvent was evaporated in vacuo. The residue was dissolved in water and passed through a column of "Amberlite" 1R-120 (Na+) resin. Removal of water gave the crude sodium salt which was chromatographed on silica eluting with 10% methanol in chloroform to give the sodium salt of the title compound, 1.14 g, 25%, $\nu_{max}$. ($CH_2Cl_2$) 1770, 1730, 1200 cm$^{-1}$, δ ($CDCl_3$), 0.92 (3H, m, $CH_3$), 1.34 (10H, m, 2×2$CH_3$, 2×$CH_2$), 3.47 (3H, s, $OCH_3$), 3.56 (1H, m, CHCONH), 4.63 (1H, bs, 3H), 5.23 (2H, s, Ph$CH_2$) 5.65 (1H, s, 5H), 7.47 (5H, s, Ph), 9.16 (1H, s, CONH).

(b) Disodium 6,α-methoxy-6,β-(sulphopentanoamido)penicillanate

Benzyl 6,α-methoxy-6,β-(2-sulphopentanoamido)-penicillanate sodium salt (1.14 g, 2.18 mmol) in water (15 ml) containing sodium bicarbonate (0.18 g, 2.18 mmol) was hydrogenated in the presence of 10% palladium on carbon (2.2 g) for six hours. The catalyst was filtered off and the filtrate evaporated to give the title compound, 0.82 g, 43%, $\nu_{max}$. (Nujol) 3700–2800, 1760, 1670, 1600, 1270 cm$^{-1}$, δ ($D_2O$) 0.97 (3H, t, J 7 Hz, $CH_3$), 1.51 (8H, s, 2×2$CH_3$, 2$CH_2$), 1.95 (2H, m, $CH_2$), 3.57, 3.60 (3H, 2×s, $OCH_3$), 3.6–4.1 (1H, m, CHCONH), 4.36 (1H, s, 3H), 5.63 (1H, s, 5H).

The following compounds were prepared as for 6,α-Methoxy-6,β-(2-Sulpho)pentanoamido penicillanic acid.

EXAMPLE 15

6,α-Methoxy-6,β-(2-sulpho)propanoamido penicillanic acid

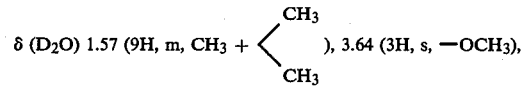

δ ($D_2O$) 1.57 (9H, m, $CH_3$ + ), 3.64 (3H, s, —$OCH_3$), 3.62–4.2 (1H, m, CH), 4.40 (1H, s, 3H), 5.61 (1H, s, 5H). $\nu_{max}$. (nujol) 1760 cm$^{-1}$.

EXAMPLE 16

6,α-Methoxy-6,β-(2-sulpho)hexanoamido penicillanic acid

δ($D_2O$) 0.87 (3H, m, $CH_3$), 1.48 (10H, s, covering multiplet,

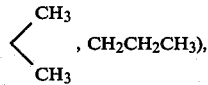, $CH_2CH_2CH_3$), 1.93 (2H, m, $CH_2CH$), 3.65 3.71 (3H, 2s,-$OCH_3$), 3.6–4.0 (1H, m CH), 4.33 (1H, s, 3H), 5.60 (1H, s, 5H).

EXAMPLE 17

6,α-Methoxy-6,β-(2-sulpho)butyramido penicillanic acid

δ($D_2O$) 1.03 (3H, t, J7 Hz, $CH_3$),

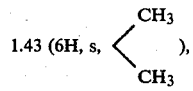

1.98 (2H, m, $CH_2$), 3.51 (2H, s, —$OCH_3$), 3.5–3.9 (1H, m, CH), 4.25 (1H, s, 3H), 5.50 (1H s, 5H). $\nu_{max}$. (nujol) 1760 cm$^{-1}$.

EXAMPLE 18

6,α-Methoxy-6,β-(4-methyl-2-sulpho)butyramido penicillanic acid

δ($D_2O$) 1.00 (6H, d, ($CH_3$)$_2$),

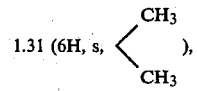

1.9–2.4 (1H, m, CH), 3.33, 3.38 (3H, 2s, $OCH_3$), 3.47, 3.55 (1H, 2s, CH), 4.12 (1H, s, 3H), 5.38 (1H, s, 5H). $\nu_{max}$. (nujol) 1760 cm$^{-1}$.

EXAMPLE 19

Disodium 6,α-methoxy-6,β-[2-(4-nitrophenyl)-2-sulphoacetamido]penicillanate

Benzyl 6,α-methoxy-6,β-[2-(4-nitrophenyl)-2-sulphoacetamido]-penicillanate sodium salt (1.41 g) in water (50 ml) was stirred and maintained at pH 10.0 with N sodium hydroxide solution for two hours. 'Amberlite' IR 120 (H) resin was added to pH 5.5, the solution washed with ether (2×20 ml) and freeze dried to a pale brown solid, 1.29 g. This was subjected to chromatography on silica eluting with n-butanol, ethanol and water (4:1:1). The fractions containing the product were bulked together and evaporated to give the title compound, 0.30 g, 24% yield, $\nu_{max}$. (KBr) 1770, 1685, 1600, 1520, 1350, 1210 and 1040 cm$^{-1}$, δ[($CD_3$)SO]1.2–1.5 (6H, m, 2×2$CH_3$), 3.40, 3.44 (3H, 2×s, $OCH_3$), 3.92, 4.00 (1H, 2×s, 3H), 4.73, 5.04 (1H, 2×s, CHCONH), 5.30, 5.37 (1H, 3×s, 5H), 7.6–8.2 (4H, m, Ar), 9.38, 9.47 (1H, 2×s, CONH).

EXAMPLE 20

6,α-Methoxy-6,β-[2-(3-methylphenyl)-2-sulphoacetamido]penicillanic acid (a) Benzyl 6,α-Methoxy-6,β-[2-(3-methylphenyl)-2-sulphoacetamido] penicillanate A solution of 2-(3-Methylphenyl)-2-sulphoacetyl chloride was prepared from 3-methylphenylacetic acid (1.5 g, 10 mmol) by the method described in Example 4a. This was used to acylate benzyl 6,β-amino-6,α-methoxypenicillanate (3.36 g, 10 mM) as described in Example 1a. The title compound was isolated as its sodium salt (1.2 g 21%) $\nu_{max}$.($CHCl_3$), 3670, 1775, 1740, 1680 cm$^{-1}$, δ[($CD_3$)$_2$SO/$D_2O$], 1.45 (6H, 6s, 2×2$CH_3$), 2.42 (3H, s, $CH_3$), 3.62, 3.74 (3H, 2×s, $OCH_3$), 4.61 (1H, 6s, 3H), 5.05, 5.35 (1H, 2×s, CHCONH), 5.35 (2H, s, O$CH_2$Ph), 5.70 (1H, s, 5H), 7.55 (9H, 6s, Ar).

(b) Disodium 6,α-Methoxy-6,β-[2-(3-methylphenyl)-2-sulphoacetamido] penicillanate Benzyl 6,α-methoxy-6,β-[2-(4-methylphenyl)-2-sulphoacetamido] penicillanate (0.57 g, 1.0 mmol) was hydrogenated in water (30 ml) containing 10% palladium on charcoal and one equivalent of sodium bicarbonate for four hours. After filtering off the catalyst the solution was freeze dried to yield the title compound as a white foam (0.47 g, 92%). $\nu_{max}$. (KBr) 1765, 1670, 1610 cm$^{-1}$, $\delta$[(CD$_3$)$_2$SO] 1.38 (6H, 6s, 2×2CH$_3$), 2.27 (3H, s, CH$_3$), 3.42, 3.70 (3H, 2×s, OCH$_3$), 3.70, 4.00 (1H, 2×s, 3H), 4.43, 4.70 (1H, 2×s, CHCONH), 5.20, 5.36 (1H, 2×s, 5H), 7.00–7.55 (4H, m, Ar), 9.37 (1H, 6s, CHCONH).

EXAMPLE 21

6,β-[2-Chlorophenyl)-2-sulphoacetamido]-6,α-methoxypenicillanic acid

(a) Benzyl 6,β-[2-chlorophenyl)-2-sulphoacetamido]-6,α-methoxypenicillanate

The sodium salt of the title compound was prepared from 2-(4-chlorophenyl)-2-sulphoacetyl chloride (2.69 g, 10 mmol) and benzyl 6,β-amino-6,α-methoxyenicillanate (3.36 g, 10 mmol) by the method described in Example 1a. Yield 1.83 g, 30%. $\nu_{max}$. (CHCl$_3$) 3700–2900, 1775, 1740, 1670 cm$^{-1}$, $\delta$[(CD$_3$)$_2$CO] 1.26 (6H, bs, 2×CH$_3$), 3.54, 3.60 (3H, 2×s, OCH$_3$), 4.48, 4.56 (1H, 2×s, 3H), 4.88, 511 (1H, 2×s, CHCONH), 5.24 (2H, s, OCH$_2$Ph), 5.52 (1H, s, 5H), 7.1–8.0(9H, m, Ar), 9.1 (1H, bs, CHCONH).

(b) Disodium 6,β-[2-(4-chlorophenyl)-2-sulphoacetamido]-6,α-methoxypenicillanate Prepared by hydrogenation of benzyl 6,β-[2-(4-chlorophenyl)-2-sulphoacetamido]-6,α-methoxypenicillanate (1.0 g, 1.7 mmol) using the method described in Example 1c. Yield 0.58 g, 65%. $\nu_{max}$. (KBr) 3650–2800, 1770, 1680, 1610 cm$^{-1}$. $\delta$[(CD$_3$)$_2$SO], 1.36 (6H, bs, 2×2CH$_3$), 3.40 (3H, bs, OCH$_3$), 3.90, 3.94 (1H, 2×s, 3H). 4.46, 4.78 (1H, 2×s, CHCONH, 5.28, 5.34 (1H, 2×s, 4H), 7.15–7.65 (4H, m, Ar), 9.32, 9.40 (1H, 2×bs, CHCONH).

EXAMPLE 22

6,α-Methoxy-6,β-[2-(4-trifluoromethylphenyl)-2-sulphoacetamido] penicillanic acid

(a) Benzyl 6,α-methocy-6,β-[2-(4-trifluoromethylphenyl)-2-sulphoacetamido penicillanate The sodium salt of the title compound was prepared from 2-(4-trifluoromethylphenyl)-2-sulphoacetyl chloride (3.02 g, 10 mmol) and benzyl 6,β-amino-6,α-methoxypenicillanate (3.36 g, 10 mmol) using the method described in Example 1a. Yield 1.73 g, 28%. $\nu_{max}$. (CHCl$_3$) 3650–2900, 1775, 1740, 1680 cm$^{-1}$, $\delta$[(CD$_3$)$_2$CO], 1.1–1.6 (6H, bs, 2×2CH$_3$), 3.21, 3.26 (3H, 2×s, OCH$_3$), 4.51, 4.56 (1H, 2×s, 3H). 5.23 (3H, bs, OCH$_2$Ph, CHCONH), 5.56 (1H, bs, 5H), 7.1–8.15 (9H, m, Ar) 9.45 (1H, bs, CHCONH).

(b) Disodium 6,α-methoxy-6,β-[2-(4-trifluoromethylphenyl)-2-sulphoacetamido]penicillanate The title compound was prepared by hydrogenation of benzyl 6,α-methoxy-6,β-[2-(4-trifluoromethylphenyl)-2-sulphoacetamido]penicillanate (1.07 g, 1.7 mmol) using the method described in Example 1c. Yield 0.72 g, 76%. $\nu_{max}$. (KBr) 3650–2800, 1770, 1685, 1620 cm $^{-1}$. $\delta$[(CD$_3$)$_2$SO], 1.34 (6H, bs, 2×2CH$_3$), 3.33 (3H, s, OCH$_3$), 4.01, 4.06 (1H, 2×s, 3H), 4.62, 4.93 (1H, 2×s, CHCONH), 5.29, 5.34 (1H, 2×s, 5H), 7.45 (4H, bs, Ar), 9.50, 9.56 (1H, 2×bs, CHCONH).

EXAMPLE 23

6,β-[2-(3-Aminophenyl)-2-sulphoacetamido]-6,α-methoxypenicillanic acid

(a) Benzyl 6,α-methoxy-6,β-[2-(3-nitrophenyl)-2-sulphoacetamidopenicillanate The title compound was prepared from 2-(3-nitrophenyl)-2-sulphoacetyl chloride (1.41 g, 5 mmol) and benzyl 6,β-amino-6,α-methoxypenicillanate using the method of Example 1a. Yield 0.85 g, 28%. $\nu_{max}$. (CHCl$_3$) 1780, 1740, 1680, 1530, 1350 cm$^{-1}$. $\delta$[(CD$_3$)$_2$CO], 1.35 (6H, m, 2×2CH$_3$), 3.55, 3.60 (3H, 2×s, OCH$_3$), 4.54, 4.60 (1H, 2×s, 3H), 5.32 (3H, bs, OCH$_2$Ph, CHCONH), 5.57 (1H, s, 5H), 7.25–8.75 (9H, m, Ar), 9.48, 9.60 (1H, 2×bs, CHCONH).

(b) Disodium 6,β-[2-(3-aminophenyl)-2-sulphoacetamido]-6,α-methoxypenicillanate The title compound was prepared by hydrogenation of benzyl 6,α-methoxy-6,β-[2-(3-n trophenyl)-2-sulphoacetamido]-penicillanate (0.75 g, 1.2 mmol) by the method of Example 1d. Yield 0.47 g, 74%. $\nu_{max}$. (CHCl$_3$), 1770, 1680, 1610 cm$^{-1}$. $\delta$[(CD$_3$)$_2$SO], 1.36 (6H, bs, 2×2CH$_3$), 3.38 (3H, bs, OCH$_3$), 3.90 (1H, bs, 3H), 4.41, 4.52 (1H, 2×s, CHCONH), 5.29, 5.32 (1H, 2×s, 5H), 6.3–7.1 (4H, m, Ar), 9.25, 9.36 (1H, 2×bs, CHCONH).

| | MIC's (μg/ml) | | | | |
| --- | --- | --- | --- | --- | --- |
| | Compound of Example No | | | | |
| Organism | 1 | 4 | 6 | 8 | 9 |
| E. coli JT 4 | 25 | 10 | 125 | 25 | 25 |
| E. coli JT 425 | 10 | 10 | 50 | 25 | 10 |
| E. coli NCTC 10418 | 25 | 10 | 50 | 25 | 10 |
| Ps. aeruginosa NCTC 10662 | >100 | 25 | 500 | 50 | >100 |
| Ps. aeruginosa NCTC 10662 10$^{-2}$ | >100 | 25 | 500 | 50 | 100 |
| Ps. aeruginosa Dalgleish 10$^{-2}$ | 50 | 25 | 250 | 25 | 100 |
| S. marcescens US 32 | >100 | 25 | 125 | 100 | 50 |
| K. aerogenes A | 2.5 | 2.5 | 12.5 | 10 | 2.5 |
| E. cloacae N1 | 25 | 5 | 12.5 | 10 | 2.5 |
| P. mirabilis C 977 | 5 | 5 | 25 | 25 | 5 |
| P. mirabilis 889 | 5 | 10 | 50 | 25 | 5 |
| P. morganii | 10 | 5 | 50 | 25 | 5 |
| P. rettgeri | 10 | 6 | 12.5 | 10 | 5 |
| B. subtilis | >100 | >100 | >500 | >100 | 25 |
| S. aureus Oxford | >100 | >100 | >500 | >100 | 25 |
| S. aureus Russell | >100 | >100 | >500 | >100 | 50 |
| N. catarrhalis 1502 | — | 0.05 | 0.5 | 0.2 | <0.02 |
| S. faecalis I | >100 | >100 | >500 | >100 | >100 |
| S. pyogenes CN 10 | 50 | 25 | >500 | 25 | 5 |

I claim:

1. A compound of formula (I) or a pharmaceutically acceptable salt or in vivo hydrolyzable ester thereof:

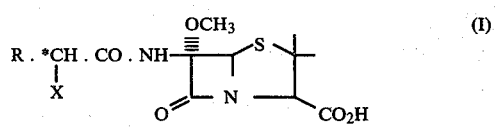

wherein R is C$_{1-6}$ alkyl; a substituted or unsubstituted 5-membered heterocyclic ring containing one or two heteroatoms selected from oxygen, sulphur and nitrogen; phenyl; mono-substituted phenyl where the substitutent is halogen, hydroxy, $C_{1-6}$ alkoxy, nitro, amino, $C_{1-6}$ alkyl, $C_{1-6}$ haloalkyl, $C_{1-6}$ alkylcarbonyloxy or $C_{1-6}$ alkyl sulphonylamino; or di-substituted phenyl where the substituents are selected from hydroxy, halogen, methoxy, acetoxy and amino; and X represents a group of formula:

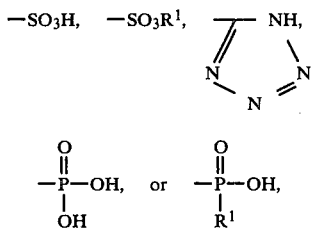

wherein $R^1$ represents $C_1$ to $C_6$ alkyl, or $C_1$ to $C_6$ alkoxy.

2. A compound as claimed in claim 1 wherein the carbon atom marked * in formula (I) is in the D configuration.

3. A compound as claimed in claim 1 wherein R is methyl, ethyl, n- or iso-propyl, n-, iso-, sec-, or tert-butyl.

4. A compound as claimed in claim 1 wherein R is phenyl; mono-substituted phenyl where the substituent is fluorine, chlorine, hydroxy, methoxy, nitro, amino, acetoxy or trifluoromethyl; or di-substituted phenyl where the substituents are selected from acetoxy or methoxy.

5. A compound as claimed in claim 1 wherein R is an optionally substituted furyl, thienyl, oxazolyl, thiazolyl isoxazolyl, isothiazolyl or imidazolyl group.

6. A compound as claimed in claim 1 wherein R is phenyl, thienyl, p-hydroxyphenyl or p-aminophenyl.

7. A compound as claimed in claim 1 wherein X is —SO₃H.

8. A compound as claimed in claim 1 selected from the group consisting of the following compounds or a pharmaceutically acceptable salt or in vivo hydrolyzable ester thereof:

6,α-methoxy-6,β(2-O-methylphosphono-2-phenylacetamido)penicillanic acid;
6,α-methoxy-6,β-[D,L-2-sulpho-2-phenylacetamido]-penicillanic acid;
6,α-methoxy-6,β-[D,L-2-sulpho-2-thien-3'-ylacetamido]penicillanic acid;
6,α-methoxy-6,β-[D,L-2-tetrazol-5'-yl-2-phenylacetamido]penicillanic acid;
6,α-methoxy-6,β-[D,L-2-phospho-2-phenylacetamido]penicillanic acid;
6,β-[D,L-2-iso-butylsulpho-2-thien-3'-ylacetamido]6-,α-methoxy penicillanic acid;
6,α-methoxy-6,β-[D,L-2-methylphosphino-2-phenylacetamido]penicillanic acid;
6,α-methoxy-6,β-[D,L-2-sulpho-2-p-amino-phenylacetamido]penicillanic acid;
6,β-[2-(4-acetoxyphenyl)-2-sulphoacetamido]-6,α-methoxypenicillanic acid;
6,β-[2-(4-hydroxyphenyl)-2-sulphoacetamido]-6,α-methoxypenicillanic acid;
6,β-[2-(2-fluorophenyl)-2-sulphoacetamido]-6,α-methoxypenicillanic acid;
6,β-[2-(2-chlorophenyl)-2-sulphoacetamido]-6,α-methoxypenicillanic acid;
6,β-[2-(4-acetoxy-3-methoxyphenyl)-2-sulphoacetamido]-6,α-methoxypenicillanic acid;
6,β-[2-(3-chlorophenyl)-2-sulphoacetamido]-6,α-methoxypenicillanic acid;
6,α-methoxy-6,β-[2-(4-methylphenyl)-2-sulphoacetamido]penicillanic acid;
6,α-methoxy-6,β-(2-sulpho)pentanoamido penicillanic acid;
6,α-methoxy-6,β-(2-sulpho)propanoamido penicillanic acid;
6,α-methoxy-6,β-(2-sulpho)hexanoamido penicillanic acid;
6,α-methoxy-6,β-(2-sulpho)butyramido penicillanic acid;
6,α-methoxy-6,β-(4-methyl-2-sulpho)butyramido penicillanic acid;
6,α-methoxy-6,β-[2-(4-nitrophenyl)-2-sulphoacetamido]penicillanic acid;
6,α-methoxy-6,β-[2-(3-methylphenyl)-2-sulphoacetamido]penicillanic acid;
6,β-[2-(4-chlorophenyl)-2-sulphoacetamido]-6,α-methoxypenicillanic acid;
6,α-methoxy-6,β-[2-(4-trifluoromethylphenyl)-2sulphoacetamido]penicillanic acid; and
6,β-[2-(3-aminophenyl)-2-sulphoacetamido]-6,α-methoxypenicillanic acid.

9. A pharmaceutical composition for the treatment of bacterial infections comprising an anti-bacterial amount of a compound as claimed in claim 1 together with a pharmaceutical carrier or excipient.

10. A pharmaceutical composition according to claim 9 wherein the antibacterial compound is selected from:
6,α-methoxy-6,β(2-O-methylphosphono-2-phenylacetamido)penicillanic acid;
6,α-methoxy-6,β-[D,L-2-sulpho-2-phenylacetamido]-penicillanic acid;
6,α-methoxy-6,β-[D,L-2-sulpho-2-thien-3'-ylacetamido]penicillanic acid;
6,α-methoxy-6,β-[D,L-2-tetrazol-5'-yl-2-phenylacetamido]penicillanic acid;
6,α-methoxy-6,β-[D,L-2-phospho-2-phenylacetamido]penicillanic acid;
6,β-[D,L-2-iso-butylsulpho-2-thien-3'-ylacetamido]6-,α-methoxy penicillanic acid;
6,α-methoxy-6,β-[D,L-2-methylphosphino-2-phenylacetamido]penicillanic acid;
6,α-methoxy-6,β-[D,L-2-sulpho-2-amino-phenylacetamido]penicillanic acid;
6,β-[2-(4-acetoxyphenyl)-2-sulphoacetamido]-6,α-methoxypenicillanic acid;
6,α-[2-(4-hydroxyphenyl)-2-sulphoacetamido]-6,α-methoxypenicillanic acid;
6,β-[2-(2-fluorophenyl)-2-sulphoacetamido]-6,α-methoxypenicillanic acid;
6,β-[2-(2-chlorophenyl)-2-sulphoacetamido]-6,α-methoxypenicillanic acid;
6,β-[2-(4-acetoxy-3-methoxyphenyl)-2-sulphoacetamido]-6,α-methoxypenicillanic acid;
6,β-[2-(3-chlorophenyl)-2-sulphoacetamido]-6,α-methoxypenicillanic acid;
6,α-methoxy-6,β-[2-(4-methylphenyl)-2-sulphoacetamido]pencillanic acid;
6,α-methoxy-6,β-(2-sulpho)pentanoamido penicillanic acid;
6,α-methoxy-6,β-(2-sulpho)propanoamido penicillanic acid;
6,α-methoxy-6,β-(2-sulpho)hexanoamido penicillanic acid;
6,α-methoxy-6,β-(2-sulpho)butyramido penicillanic acid;

6,α-methoxy-6,β-(4-methyl-2-sulpho)butyramido penicillanic acid;

6,α-methoxy-6,β-[2-(4-nitrophenyl)-2-sulphoacetamido]penicillanic acid;

6,α-methoxy-6,β-[2-(3-methylphenyl)-2-sulphoacetamido]penicillanic acid;

6,β-[2-(4-chlorophenyl)-2-sulphoacetamido]-6,α-methoxypenicillanic acid;

6,α-methoxy-6,β-[2-(4-trifluoromethylphenyl)-2-sulphoacetamido]penicillanic acid; and 6,β-[2-(3-aminophenyl)-2-sulphoacetamido]-6,α-methoxypenicillanic acid.

11. A method of treating bacterial infections which comprises administering to a host in need thereof an antibacterial amount of a composition of claim 9.

12. A method of treating bacterial infections which comprises administering to a host in need thereof an antibacterial amount of a composition of claim 10.

13. An antibacterial composition according to claim 9 wherein the compound of formula (I) is the sole therapeutic agent or further comprises a compound of formula (VI) or a pharmaceutically acceptable salt or ester thereof:

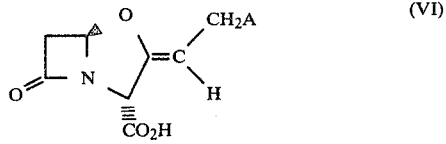

wherein A is hydroxyl, substituted hydroxyl, thiol, substituted thiol, amino, mono- or di-hydrocarbylsubstituted amino, or mono- or di-acylamino.